United States Patent
He et al.

(10) Patent No.: US 10,395,757 B2
(45) Date of Patent: Aug. 27, 2019

(54) PARENTAL GENOME ASSEMBLY METHOD

(75) Inventors: Weiming He, Shenzhen (CN); Shancen Zhao, Shenzhen (CN); Xuemei Zhang, Shenzhen (CN); Yingrui Li, Shenzhen (CN); Jun Wang, Shenzhen (CN); Jian Wang, Shenzhen (CN); Huanming Yang, Shenzhen (CN)

(73) Assignee: BGI TECH SOLUTIONS CO., LTD., Shenzhen (CN)

( * ) Notice: Subject to any disclaimer, the term of this patent is extended or adjusted under 35 U.S.C. 154(b) by 496 days.

(21) Appl. No.: 14/361,865

(22) PCT Filed: Dec. 2, 2011

(86) PCT No.: PCT/CN2011/083390
§ 371 (c)(1),
(2), (4) Date: Aug. 27, 2014

(87) PCT Pub. No.: WO2013/078684
PCT Pub. Date: Jun. 6, 2013

(65) Prior Publication Data
US 2015/0205913 A1    Jul. 23, 2015

(51) Int. Cl.
*G16B 20/00* (2019.01)
*C12Q 1/6869* (2018.01)
*C12Q 1/6895* (2018.01)
*G16C 99/00* (2019.01)

(52) U.S. Cl.
CPC ........... *G16B 20/00* (2019.02); *C12Q 1/6869* (2013.01); *C12Q 1/6895* (2013.01); *G16C 99/00* (2019.02); *C12Q 2535/122* (2013.01)

(58) Field of Classification Search
None
See application file for complete search history.

(56) References Cited

FOREIGN PATENT DOCUMENTS

CN     101504697 A    8/2009

OTHER PUBLICATIONS

Li, R. et al., De novo assembly of human genomes with massively parallel short read sequencing; Genome Research 20:265-272 (2010).
Yu, J. et al., Genetic association mapping and genome organization of maize; Current Opinion in Biotechnology 2006, 17:155-160.
Li, R. et al., "SNP detection for massively parallel whole-genome resequencing", Genome Res. 2009 19: 1124-1132 originally published online May 6, 2009.
Li, R. et al., "SOAP2: an improved ultrafast tool for short read alignment", vol. 25 No. 15, 2009, pp. 1966-1967.
Yu, J. et al., "A Draft Sequence of the Rice Genome (*Oryza sativa* L. ssp. *indica*)", Science 296, pp. 79-91 (Apr. 5, 2002).
Wei, G. et al., "A transcriptomic analysis of superhybrid rice LYP9 and its parents", PNAS, May 12, 2009, vol. 106, No. 19, pp. 7695-7701.
Agarwal, M. et al., "Advances in molecular marker techniques and their applications in plant sciences", Plant Cell Rep (2008) 27:617-631.
PCT/CN2011/083390 English Translation of International Search Report and Written Opinion dated Sep. 13, 2012, 12 pages.

*Primary Examiner* — Joseph Woitach
(74) *Attorney, Agent, or Firm* — Lathrop Gage LLP

(57) ABSTRACT

Provided is a parental genome assembly method, comprising: using the sequencing data of parental selfing line progeny population to assemble and perfect the parental genome data. Also provided is a device for implementing the method.

16 Claims, 5 Drawing Sheets
Specification includes a Sequence Listing.

| # position | BI5 | BI7 | BI8 | BI9 | BI10 | BI11 | BI12 | BI16 | BI18 |
|---|---|---|---|---|---|---|---|---|---|
| 893  | 0 0 | 1 1 | 0 1 | - 1 | 1 1 | 1 0 | 1 0 | 0 0 | 0 1 |
| 1406 | 0 0 | 1 1 | 0 1 | 1 1 | 1 1 | 1 0 | 1 0 | 0 0 | 1 1 |
| 2071 | 0 0 | 1 1 | 0 1 | 1 1 | 1 1 | 1 0 | 1 0 | 0 0 | 1 1 |
| 2717 | 0 0 | 1 1 | 0 1 | 1 1 | 1 - | 1 0 | 1 0 | 0 0 | 1 1 |
| 3330 | 0 0 | 1 1 | 0 - | 1 1 | 0 1 | 1 0 | 1 0 | 0 0 | 0 - |
| 3504 | 0 - | 1 1 | 0 1 | 1 1 | 1 1 | 1 0 | - 0 | 0 0 | 1 1 |
| 3532 | 0 0 | 1 1 | 0 1 | 1 1 | 1 1 | 1 0 | 1 - | 0 0 | 1 1 |
| 3557 | 0 0 | 1 1 | 0 1 | 1 1 | 1 1 | 1 0 | 1 0 | 0 0 | 0 1 |
| 4495 | - 0 | 1 1 | 0 1 | 1 1 | 0 1 | 1 0 | 1 0 | 0 0 | 0 1 |
| 4773 | 0 0 | 1 1 | 0 1 | - 1 | 1 1 | 1 - | 1 0 | - 0 | 1 1 |
| 4847 | 0 0 | 1 1 | 0 1 | 1 1 | 1 - | 1 0 | 1 0 | 0 0 | 1 1 |
| 5384 | 0 - | 1 1 | 0 1 | 1 1 | 0 1 | 1 0 | 1 0 | 0 0 | 0 1 |

Fig.6

| marker number | forwarding/reversing alignment | linkage group | starting point | terminating point | scaffolds | scaffold start | scaffold length |
|---|---|---|---|---|---|---|---|
| 49 | + | chr02_747m50 | 283 | 13670 | Chr02_1 | 1 | 13389 |
| 38 | + | chr02_14344m50 | 14188 | 27101 | Chr02_2 | 1 | 12902 |
| 171 | + | chr02_27088m50 | 26075 | 73296 | Chr02_3 | 1 | 47242 |
| 76 | + | chr02_73948m50 | 73621 | 96387 | Chr02_4 | 1 | 22763 |
| 44 | + | chr02_96941m50 | 96490 | 108029 | Chr02_5 | 1 | 11541 |
| 66 | + | chr02_121935m50 | 108901 | 146504 | Chr02_9 | 1 | 37896 |
| 2 | + | chr02_114898m50 | 113938 | 117989 | Chr02_6 | 1 | 4051 |
| 1 | + | chr02_119644m50 | 119232 | 120006 | Chr02_7 | 1 | 775 |
| 4 | + | chr02_121573m50 | 120697 | 122248 | Chr02_8 | 1 | 1539 |
| 1 | + | chr02_127642m50 | 126881 | 127838 | Chr02_11 | 1 | 958 |
| 1 | + | chr02_149708m50 | 149575 | 150308 | Chr02_10 | 1 | 734 |

SEQUENCE LISTING

```
<160> NUMBER OF SEQ ID NOS: 11

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
taaaataatt gtccgtcaac tt                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
ttcgacgtca accccagttc cg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic
```

```
<400> SEQUENCE: 3
ttctcatgtt tattaaaata at                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
cgaccatttc tgaatattaa aa                                              22

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ggcgaccatt taggaatatt aa                                              22

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
cgggcgacca tattaaaata at                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
ggcgggcgac ccaaggaata tt                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
cggcgggcga caatattaaa at                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
acaacggcgg gaaggaatat ta                                              22

<210> SEQ ID NO 10
```

```
<211> LENGTH: 22
<212> TYPE: DNA
<213> ORGANISM: Artificial Sequence
<220> FEATURE:
<223> OTHER INFORMATION: Synthetic

<400> SEQUENCE: 10
gagacaacgg cgtcaaggaa ta                                              22

<210> SEQ ID NO 11
<211> LENGTH: 87
<212> TYPE: DNA
<213> ORGANISM: Artificial Sequence
<220> FEATURE:
<223> OTHER INFORMATION: Synthetic

<400> SEQUENCE: 11
gagacaacgg cgggcggcca tttctcatgt ttcgacgtca aggaatttta aaataattgt     60
ctcgttcccc agttccgtca acttaca                                         87
```

PARENTAL GENOME ASSEMBLY METHOD

CROSS-REFERENCE TO RELATED APPLICATION

This application is a U.S. national phase of International application No. PCT/CN2011/083390, filed Dec. 2, 2011, the entire content of which is incorporated herein by reference.

FIELD

Embodiments of the present disclosure generally relate to fields of genetic engineering technology, genetics, and genomic bioinformatics, particularly to a method of obtaining genomes of parents, comprising obtaining and improving the genome of parents using sequencing data of inbred lines progeny population. An apparatus for implementing the method is also provided.

BACKGROUND ART

The Next-Generation DNA sequencing technology is a high-throughput sequencing technology with low cost, with a fundamental of sequencing synthesis. Taking Solexa sequencing method as an example, it comprises: firstly randomly fragmenting DNA strands using a physical method, secondly ligating a specific adaptor to an obtained DNA fragments at both ends, in which the specific adaptor has an amplification primer sequence; thirdly subjecting obtained DNA fragments ligated with the specific adaptor to sequencing. During the step of sequencing, DNA polymerase synthesizes a complementary strand of the DNA fragments to be analyzed by means of the adaptor, and obtains a base sequence by detecting fluorescence signal carrying by the newly-incorporated base, so as to obtain a sequence of the DNA fragments to be analyzed. These obtained sequences are regarded as reads. A basic process of the Solexa sequencing method may refer to, for example www.Illumine.com.

To retrieve an intact sequence of genome (for example, assembling reads into genome sequence such as chromosome sequence), the Next-Generation sequencing technology usually connects reads in a gradient way. First of all, by means of an overlapping relationship between reads, the reads are extended as much as possible (namely, connect together), to form contigs; secondly, by means of a distance relationship between reads of pair-ends in a Pair-End sequencing, different contigs having pair-end reads are connected together by adding the certain number of N in the middle, to form scaffolds. In the scaffolds, a sequential order of the contigs before and after the N region is already known, and a distance thereof in the DNA sequence is also known; finally, information of these N regions are retrieved to sequence information by "gap closure" methods. One of the "gap closure" methods is that: finding a pair-end reads, in which one end thereof is located in the known sequence of the scaffolds, and the other end thereof is located in the N region of the scaffolds; calculating all reads located in the N region; and then performing local assembly by the overlapping relationship to obtain sequence information of the N region. A general protocol of sequence connecting may refer to, for example Li, R. et al. De novo assembly of human genomes with massively parallel short read sequencing. *Genome Res* 20, 265-72 (2010).

Although it may connect sequencing data (namely, reads) of the Next-Generation sequencing technology using known software, since the reads obtained by the Next-Generation sequencing technology generally have a relatively short read length (commonly just 100 bp), there is a certain limitation for connecting sequencing data: it is very hard to assemble reads into genome sequence such as chromosome sequence simply relying on assembly software.

Therefore, it is urgent in the art to improve the method of assembling reads, to further optimize an assembling result of sequencing data, and increase the accuracy of the assembling result (namely, obtaining high-accurate genome sequence). Particularly, the present disclosure also provides a new method of obtaining and improving genomes of parents using sequencing data of inbred lines progeny population.

SUMMARY

In the present disclosure, unless otherwise stated, scientific and technical terms used herein have commonly-understood meanings by those skilled in the art. All terms in genetics, molecular biology, nucleic acid chemistry and bioinformatics are widely-used term in corresponding fields, and all relative experimentally-operative steps are conventional steps in corresponding fields. Meanwhile, in order to better understand the present disclosure, definitions and explanations of the relative terms will be provided below.

The term "genetic map" used herein is also known as a linkage map or a chromosome map, showing a relative distance (namely, genetic distance) between genes or genetic marker, other than showing a physical distance of gene or genetic marker in chromosome. In the genetic map, the genetic distance is used for describing a position relationship between the genes or the genetic markers, which is calculated using a recombination rate. Generally, the longer distance between two genes or genetic markers in one chromosome, the greater probability of the recombination occurring during meiosis, the smaller probability of the common heredity. In accordance with a genetic segregation of genetic characters in progeny, a recombination rate thereof can be calculated, so as to calculate a genetic distance thereof in the genetic map. When the recombination rate of two genes or genetic markers is 1%, the genetic distance thereof is defined as 1 cm (centimorgan).

Currently, commonly-used genetic markers mainly comprise: restriction fragment length polymorphism (RFLP), simple sequence repeats (SSR), sequence-tagged site (STS) and single nucleotide polymorphism (SNP). These genetic markers are all well-known to those skilled in the art, which may refer to, for example Agarwal, M., Shrivastava, N. & Padh, H. Advances in molecular marker techniques and their applications in plant sciences. *Plant cell reports* 27, 617-631 (2008).

The term "SNP" used herein refers to DNA sequence polymorphism resulted from a variation of a single nucleotide at the genomic level. SNP is one of the most common types in bio-genetic variation, being more than 90% of all known polymorphism. The term "SNP site" used herein refers to a site having single nucleotide polymorphism. The SNP site extensively presents in genomes of various species. Particularly, in human genome, based on one SNP site in every 500 to 1000 bases in average, the total number of SNP site is estimated up to 3 million or even more. As used herein, when referring to individual SNP site, it indicates that the genome of such individual has different bases at this site relative to a reference sequence.

The term "homozygous SNP site" used herein refers to an SNP site, at which all aligning sequences show an identical base, and such base is different with a base in the reference sequence. For example, if the reference sequence has a base G at a certain SNP site, while all aligning sequences have a base A at the certain SNP site, then the certain SNP site is regarded as a homozygous SNP site (See FIG. 1).

The term "reads" used herein refers to sequencing data obtained by sequencing by various sequencing methods. For example, the Next-Generation sequencing method such as Solexa sequencing method is an optimal method for providing reads. Particularly, the term "reads" used herein preferably refers to sequencing data obtained using the Next-Generation sequencing method such as Solexa sequencing method. The term "paired reads" refers to reads obtained by following method: when subjecting DNA fragments to sequencing using Solexa sequencing method, ligating an adaptor to the DNA fragments at both ends, then subjecting such DNA fragments to sequencing using the adaptor respectively from both ends, accordingly to obtain paired reads. The paired reads are regarded as having a pairwise relationship.

The term "scaffolds" used herein refers to fragments obtained by connecting reads in accordance to an overlapping relationship and a physical distance between reads.

The expression "obtaining genome" used herein refers to obtaining sequence information of genome.

The expression "improving genome" used herein refers to making the obtained genome sequence near to the authentic genome sequence as much as possible (namely, improve the accuracy of the obtained genome sequence), which includes but not limited to, determining a sequence of N region in the obtained genome sequence and correcting an error base in the obtained genome, etc. The term "accuracy" used herein is used to describe a pairwise level between genome sequence obtained by assembling and the authentic genome sequence.

The term "inbred lines progeny population" used herein refers to obtaining progeny population of parents by following steps: cross-fertilizing parents to obtain a first generation; self-fertilizing the first generation for one or more generations (for example, 2 generations, 3 generations, 4 generations, 5 generations, 6 generations, 7 generations, 8 generations, 9 generations, 10 generations, 12 generations, 14 generations, 16 generations, 20 generations, or more generations) to obtain the inbred lines progeny population. As used herein, an individual in the inbred lines progeny population is regarded as inbred lines progeny individual.

The expression "assembling reads (or scaffolds)" used herein refers to arranging every read (or scaffold) according to a relative position relationship in the genome. The term "arranging" used herein not only refers to arranging every read according to a relative position relationship, but also refer to determining a connecting direction of every read.

The term "consensus genotype sequence" refers to such sequences having a length same as the reference sequence (for example, reference genome), and except for SNP site, of which the genome sequence information is consistent with the reference sequence at all other sites. Any known SNP software may be used, to determine an SNP site in sequencing data of an individual and a genotype at the SNP site by means of Bayesiam Model. Generally, sequencing data of an individual are aligned to a reference genome, to obtain the consensus genotype sequence of the individual.

"Genotype" at a certain site used herein refers to a base included in a genome at the site. Thus, the genotype of individual A being different to (or same with) the genotype of individual B at a certain site indicates that genome of the individual A includes a different (or same) base to genome of the individual B at that site.

The term "segregation site" used herein refers to such site, at which a difference presents in the genome sequences of two parents (namely, having different base).

The term "genome drafts" used herein refers to genomes of parents obtained by directly assembling scaffolds of parent, which is not improved using sequencing data (namely, reads) of inbred lines progeny population. Relative to the genome obtained by the assembling method of the present disclosure, the genome draft has an effective length being relatively short, which comprises many N regions and has a low accuracy. The term "N region" used herein refers to an unknown region in the genome.

The term "single base correction" used herein refers to correcting a base of a reference sequence (e.g., genome of parent) at a homozygous SNP site using a base of an aligning sequence (e.g., reads of inbred lines progeny population) at the homozygous SNP site.

The term "sequencing depth" used herein refers to a fold of the amount of sequencing data relative to the amount of whole genome data. For example, sequencing depth is 2 refers to the amount of sequencing data is 2 fold of the amount of whole genome data.

The term "unit" or "subunit" used herein refers to a hardware comprising software and/or algorithm which are/is executable to achieve intended purpose. Such hardware is well-known in the art, and is able to be integrated into devices such as computer, servers, and etc.

In the present disclosure, inventors innovatively uses sequencing data of inbred lines progeny population in obtaining and improving genomes of parents, so as to provide a new method of obtaining genomes of parents, which greatly improves accuracy of assembled genomes of parents.

Particularly, the present disclosure is at least partly based on following principles: genomes of inbred lines progeny population entirely derives from two parents, and genomic information carried by reads of these inbred lines progeny population is exactly the corresponding genomic information carried by reads of the derived parents. Thus, after determining parent source of the reads of the inbred lines progeny population, these reads may be used in obtaining and improving genomes of parents derived, which greatly improves accuracy of genome of parents.

Therefore, in one aspect, the present disclosure provided a method of obtaining genomes of parents, in which the parents are parent A and parent B, and the method comprises following steps:

a) providing reads and scaffolds, comprising:

a1) subjecting the parents to a whole genome sequencing respectively, to provide the reads deriving from the parents, wherein the reads of the parent A constitute a database A0, the reads of the parent B constitute a database B0;

a2) connecting the reads in the database A0 into scaffolds of the parent A and connecting the reads in the database B0 into scaffolds of the parent B, wherein the scaffolds of the parent A constitute a database A1, the scaffolds of the parent B constitute a database B1;

a3) providing inbred lines progeny population of the parents, wherein the inbred lines progeny population comprises at least one of inbred lines progeny individuals; and a4) subjecting every inbred lines progeny individual to the whole genome sequencing respectively, to provide paired reads of every inbred lines progeny individual, wherein the paired reads constitute a database C, namely, reads of the inbred lines progeny population;

b) identifying a segregation site of the parents, comprising:
   b1) when other genomes of a species to which the parents belong are known, selecting a known genome as a reference sequence, and aligning the reads in the database A0 and the database B0 to the reference sequence respectively, to obtain consensus genotype sequences of the parent A and the parent B respectively; comparing the consensus genotype sequences of the parent A and the parent B, to identify a different site presenting in the parents, namely, the segregation site, determining a genotype of the parent A and parent B at the segregation site respectively, and recording a position of the segregation site in the reference sequence; or
   b2) when other genomes of a species to which the parents belong are unknown, selecting and assembling the reads deriving from one of the parents into an initial genome sequence as a reference sequence, aligning the reads deriving from the other one of the parents to the reference sequence, to obtain consensus genotype sequences of the parents respectively; comparing the consensus genotype sequences of the parent A and the parent B, to identify a different site presenting in the parents, namely, the segregation site, respectively determining a genotype of the parent A and the parent B at the segregation site, recording a position of the segregation site in the reference sequence;

c) obtaining genome drafts of the parents, comprising:
   c1) selecting a sequence located 10 bp to 90 bp before and/or 10 bp to 90 bp after the segregation site in the consensus genotype sequence of the parent A and the parent B as a marker sequence of the parent A and the parent B respectively, and recording a position of the marker sequence in the reference sequence in step b);
   c2) locating the marker sequence of the parent A on the scaffolds in the database A1 and locating the marker sequence of the parent B on the scaffolds in the database B1 using global alignment software, wherein the marker sequence should be uniquely and completely accurately aligned to the scaffolds located thereof; and
   c3) according to the position of the marker sequence in the reference sequence, arranging the scaffolds comprising the marker sequence in the database A1 and the database B1 in order, wherein an unknown sequence between two neighboring scaffolds is represented as an N-region, to obtain the genome drafts of the parent A and the parent B;

d) classifying the reads in the database C, comprising:
   d1) aligning the reads in the database C to the reference sequence in step b), to determine whether these reads comprise the segregation site recorded in the reference sequence, and to determine a genotype thereof at the segregation site;
   d2) based on the respective genotype of the parent A and the parent B at the segregation site in step d1), classifying the reads in the database C into 3 categories:
      i) reads of which the genotype at the segregation site is consistent with the genotype of the parent A, derives from the parent A, and constitute a database A2;
      ii) reads of which the genotype at the segregation site is consistent with the genotype of the parent B, derives from the parent B, and constitute a database B2;
      iii) undistinguishable reads; and
   d3) connecting the reads in the database A2 into new scaffolds of the parent A, to constitute a database A3; connecting the reads in the database B2 into new scaffolds of the parent B, to constitute a database B3, e) obtaining the genome of the parent A and the parent B by following steps:
   e1) improving the genome drafts of the parent A using the scaffolds in the database A3 and improving the genome drafts of the parent B using the scaffolds in the database B3, comprising:
      e1-1) selecting a continuous sequence having a length of 50 bp to 150 bp within 200 bp to 400 bp of a non-N-region sequence in the genome drafts of the parent A and the parent B as a signing sequence respectively, and recording a position of the signing sequence in the genome drafts;
      e1-2) locating the signing sequence of the parent A on the scaffolds in the database A3, locating the signing sequence of the parent B on the scaffolds in the database B3, wherein the signing sequence should be uniquely and completely accurately aligned to the scaffolds located thereof; and
      e1-3) based on the position of the signing sequence in the genome drafts,
         locating the scaffolds comprising the signing sequence in the database A3 into the position of the signing sequence in the genome drafts of the parent A,
         locating the scaffolds comprising the signing sequence in the database B3 into the position of the signing sequence in the genome drafts of the parent B, and
         filing up the N region in the genome drafts using the scaffolds comprising the signing sequence; and/or
   e2) improving the genome drafts of the parent A using a pairwise relationship between the reads in the database A2 and improving the genome drafts of the parent B using a pairwise relationship between the reads in the database B2, comprising:
      e2-1) finding paired reads having the pairwise relationship in the database A2, wherein one of the paired reads is located in the non-N region in the genome draft of the parent A, while at least one part of the other one of the paired reads is located in the N region; then filling up the N region in the genome draft of the parent A using the other one of the paired reads; and
      e2-2) finding paired reads having the pairwise relationship in the database B2, wherein one of the paired reads is located in the non-N region in the genome draft of the parent B, while at least one part of the other one of the paired reads is located in the N region; then filling up the N region in the genome draft of the parent B using the other one of the paired reads;

f) optionally, subjecting the genomes of the parents in step e) to a single base correction, comprising:
   f1) aligning the reads in the database A2 to the genome of the parent A, wherein the genome of the parent A is selected as a reference sequence; finding a homozygous SNP site; correcting a base of the genome of the parent A at the homozygous SNP site using a base of the reads at the homozygous SNP site; and/or
   f2) aligning the reads in the database B2 to the genome of the parent B, wherein the genome of the parent A is selected as a third reference sequence; finding a homozygous SNP site; correcting a base of the genome of the parent B at the homozygous SNP site using a base of the reads at the homozygous SNP site; and g) optionally, performing following steps:
  g1) aligning the scaffolds being not integrated into the genome draft of the parent A in the database A1 in step c3) to the genome of the parent A obtained in step f), wherein if the scaffolds are able to be located in the genome, the scaffolds are further used to obtain the genome; and/or
  g2) aligning the scaffolds being not integrated into the genome draft of the parent B in the database B1 in step c3) to the genome of the parent B obtained in step f), wherein if the scaffolds are able to be located in the genome, the scaffolds are further used to obtain the genome.

In one preferred embodiment, the parent is a plant, for example spermatophyte, such as a monocotyledon and a dicotyledon, for example rice, wheat, cotton and etc.

In one preferred embodiment, in step a1), the parents have a whole genome sequencing depth of at least 5×, preferably at least 10×, for example at least 30×. In one preferred embodiment, in step a1), the parents are subjected to the whole genome sequencing by a Solexa sequencing method.

In one preferred embodiment, in step a2), the reads in the database A0 are connected into the scaffolds of the parent A using SOAPDenovo software; and the reads in the database B0 are connected into the scaffolds of the parent B using SOAPDenovo software.

In one preferred embodiment, in step a3), the inbred lines progeny population comprises at least 10, at least 20, at least 30, at least 40, at least 50, at least 60, at least 70, at least 80, at least 90, at least 100, at least 150, at least 200 or more of the inbred lines progeny individuals.

In one preferred embodiment, in step a4), every inbred lines progeny individual has a whole genome sequencing depth of at least 2×, for example at least 4×. In one preferred embodiment, in step a4), every inbred lines progeny individual is subjected to the whole genome sequencing by a Solexa sequencing method.

In one preferred embodiment, in step b1) or b2), the reads are aligned to the reference sequence using short sequence alignment software such as SOAP or bwa; analyzing an aligned result using SOAPsnp software, to obtain the consensus genotype sequence of the parent.

In one preferred embodiment, in step b2), methods of assembling reads of parents into an initial genome sequence are known to people skilled in the art. For example, a genetic map may be used to obtain the initial genome sequence, referring to: for example PCT/CN2011/076840 (which is incorporated herein by reference), which specifically describes a method of constructing a genetic map using an SNP site and a method of assembling individual reads into an initial genome sequence using the constructed genetic map. The initial genome sequence used herein refers to a genome sequence of which sequencing information needs to be further improved. It should note that in step b2), one of the consensus genotype sequence of the parents is the reference sequence, while the other one of the consensus genotype sequence of the parents is obtained by being aligned to the reference sequence.

In one preferred embodiment, in step c1), sequences located 50 bp before and 50 bp after the segregation site are selected as the marker sequence, namely, the marker sequence has a length of 101 bp (50 bp before the segregation site plus the segregation site plus 50 bp after the segregation site). In one preferred embodiment, in step c2), the global alignment software is Blastn. In one preferred embodiment, the assembly of the genome drafts of the parents in step c) is shown in FIG. 3.

In one preferred embodiment, in step d1), short sequence alignment software such as SOAP or bwa is used for aligning the reads to the reference sequence; and SOAPsnp software is used for analyzing the aligned result, so as to determine whether these reads comprise the segregation site recorded in the reference sequence, and to determine a genotype thereof at the segregation site;

In one preferred embodiment, in step d3), the reads in the database A2 are connected to the new scaffolds of the parent A using SOAPDenovo software; and the reads in the database B2 are connected to the new scaffolds of the parent B using SOAPDenovo software.

In one preferred embodiment, in the step e1-1), a continuous sequence having a length of 100 bp within 300 bp of the non-N region sequence in the genome drafts is selected as the signing sequence. In one preferred embodiment, the procedure described in step e1) is shown in FIG. 4. In one preferred embodiment, the procedure described in step e2) is shown in FIG. 5.

In another aspect, the present disclosure provides an apparatus for obtaining genomes of parents, in which the parents consist of parent A and parent B, and the apparatus comprises:

1) a sequencing unit, configured to sequence an individual, to provide reads of the individual;
2) a data storing unit, configured to receive data and store the data in a database;
3) a data processing unit comprising a first subunit and other subunits, configured to process the data
  wherein the first subunit comprises:
    first software, configured to connect the reads into scaffolds, for example SOAPDenovo;
    second software, configured to align the reads to a reference sequence, for example SOAP or bwa;
    third software, configured to analyze an aligned result, for example SOAPsnp;
    global alignment software, for example Blastn;
  wherein the other subunits comprises:
    a second subunit, configured to identify a segregation site of parents;
    a third subunit, configured to obtain genome drafts of the parents;
    a fourth subunit, configured to determine a parent-of-origin of the reads of inbred lines progeny individuals; and
    a fifth subunit for implementing the step e), f) and/or g) in the method described above.

In one preferred embodiment, the individuals for sequencing comprise a parent A, a parent B and inbred lines progeny individuals.

In one preferred embodiment, the database comprises at least one or more database selected from followings:
  a database A0, configured to store reads of the parent A;
  a database B0, configured to store reads of the parent B;
  a database C, configured to store reads of the inbred lines progeny individuals;
  a database A1, configured to store scaffolds of the parent A;
  a database B1, configured to store scaffolds of the parent B;
  a database A2, configured to store reads of the parent A in the database C;
  a database B2, configured to store reads of the parent B in the database C;
  a database A3, configured to store scaffolds connected from the reads in the database A2;

a database B3, configured to store scaffolds connected from the reads in the database B2;

a database X1, configured to store a genome draft of the parent A;

a database Y1, configured to store a genome draft of the parent B;

a database X2, configured to store a genome of the parent A;

a database Y2, configured to store a genome of the parent B; and a database M, configured to store the reference sequence.

Advantageous Effects of the Present Disclosure

The present disclosure innovatively uses sequencing data of inbred lines progeny population in obtaining genomes of parents, so as to provide a new method of obtaining genomes of parents. Comparing to prior art, the technical solution of the present disclosure significantly improves accuracy of assembled genomes of parents, which providing a more powerful tools for genomics research.

Reference will be made in detail to embodiments of the present disclosure; however it shall be appreciated by those skilled in the art that following figures and examples are explanatory, and used to generally understand the present disclosure, but shall not be construed to limit the present disclosure. According to figures and following detailed description in preferred embodiments, various purposes and advantages of the present disclosure will become apparent to those skilled in the art.

BRIEF DESCRIPTION OF THE DRAWINGS

FIG. 6 schematically illustrates a parent-of-origin of a genotype of every individual in progeny population at a segregation site, in which 0 represents deriving from parent 9311 rice, 1 represents deriving from parent Pa64 rice, —represents being unknown and the first line (namely, BI4-BI18) represents No. of progeny individuals, the first column represents a physical position of the segregation site in a genome sequence.

DETAILED DESCRIPTION

Figure 1:
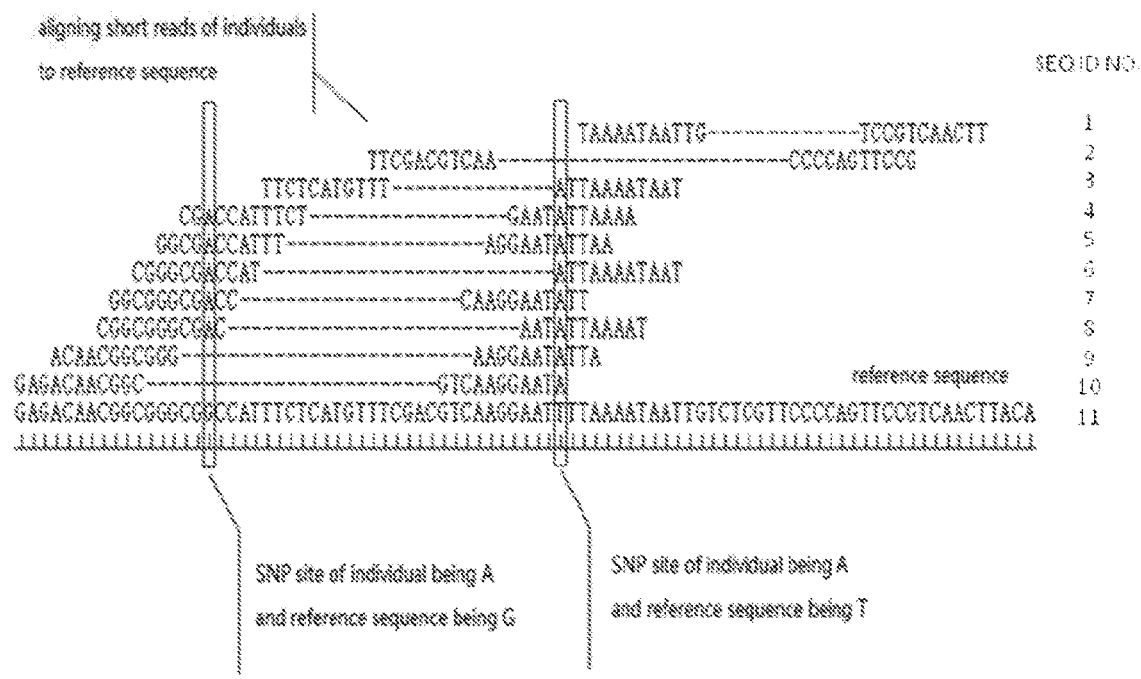
FIG. 1 schematically illustrates a method of determining an SNP site by aligning individual reads to a reference sequence, which shows an SNP site of base A in the individual reads and of base G in the reference sequence.

Reference will be made in detail combining with figures and examples, to make the purpose, technical solution and advantages of the present disclosure more clear and understood. It shall understand that specific examples described herein are explanatory, illustrative, and used to generally understand the present disclosure, and shall not be construed to limit the present disclosure.

Following examples, taking rice as an example, schematically describe a method of obtaining genomes of parent 9311 and parent PA64 using sequencing data of inbred lines progeny population of parents.

Example 1 Generation of Inbred Lines Progeny Population of Rice 9311 rice (Yu, J. et al. A draft sequence of the rice genome (*Oryza sativa* L. ssp. indica). *Science* 296, 79 (2002)) was subjected to cross-fertilization with PA64 rice Wei, G. et al. A transcriptomic analysis of superhybrid rice LYP9 and its parents. *Proc Natl Acad Sci USA* 106, 7695-701 (2009)), to generate F1 generation. Then the F1 generation was subjected to self-fertilization for 16 generations, to obtain inbred lines progeny population of rice.

Example 2 Generation of Reads of Parents and Inbred Lines Progeny Population 132 progeny individuals were selected from progeny population after 16 generations self-fertilization. According to specification of manufacturer, using Solexa sequencing platform (Illumina Company), the selected progeny individuals were subjected to individual genome sequencing having a sequencing depth of 2× (namely, the amount of sequencing data was twice as that of genome), so as to provide genome sequencing data of progeny individuals (reads). Using the same method, the genomes of parents (9311 rice and PA64 rice) were subjected to sequencing having a respective sequencing depth of 10× (namely, the amount of sequencing data was 10 folds as that of genome).

Example 3 Generation of Scaffolds of Parents (9311 Rice and PA64 Rice)

Methods being well-known in the art were used to, such as SoapDenovo assembly software (soap.genomics.org.cn/soapdenovo.html), subject reads of 9311 rice and PA64 rice to connecting respectively, to obtain scaffolds of 9311 rice and PA64 rice respectively.

Besides, scaffolds of 9311 rice and PA64 rice which had been published could also be used. For example, in 2002, genomes of 9311 rice and PA64 rice had been subjected to sequencing having a sequencing depth of 6.02× using Sanger sequencing platform, and the obtained reads had been connected into scaffolds using RePS assembly software (genome.cshlp.org/content/12/5/824.full) being well-known in the art, sequence information of these scaffolds could refer to Yu, Hu et al. 2002. These known scaffolds were used in following examples.

Example 4 Identification of a Segregation Site of Parents (9311 Rice and PA64 Rice)

Taking known rice genome Tiger (rapdb.dna.affrc.go.jp) as a reference sequence, using alignment software such as SOAP (Li, R. et al. SOAP2: an improved ultrafast tool for short read alignment. Bioinformatics 25, 1966-7 (2009)), reads of parents (10× Solexa data) were aligned to the reference sequence. During aligning, a default parameter of SOAP software was used, without allowance of a vacancy, and allowing not more than 5 mismatches.

SOAPsnp software (See for example Li, R. et al. SNP detection for massively parallel whole-genome resequencing. Genome Research 19, 1124 (2009) or SOAP.genomics.org.cn/SOAPsnp.html) was used to analyze the aligned result obtained by SOAP software, to find an SNP site of parents relative to the reference sequence and obtain consensus genotype sequence of parents. FIG. 1 schematically illustrated a method of determining an SNP site by aligning individual reads to a reference sequence, which shows an SNP site of base A in the individual reads and of base G in the reference sequence. In particular, FIG. 1 showed an SNP site of base A in an individual reads and of base G in the reference sequence and an SNP site of base A in an individual reads and of base T in the reference sequence.

Comparing the consensus genotype sequence of the parents one by one, to identify the segregation site of parents at the SNP site, namely, a different site presents in parents. Sequence located 50 bp before and 50 bp after the segregation site in the consensus genotype sequence were selected as a marker sequence. The statistical results of the SNP site and the segregation site of parents were shown in Table 1.

TABLE 1

The statistical results of the SNP site and the segregation site of parents

| SNP site of 9311 rice | SNP site of PA64 rice | segregation site of parents | total length of the marker sequence |
|---|---|---|---|
| 711813 | 542113 | 485468 | 49.03 Mbp |

The statistical results in Table 1 showed that, segregation site markers of parents not only had a huge amount, but also equally distributed in the entire genome basically. In addition, these segregation site markers basically covered the entire genome, so as to be used in assembling scaffolds into genome sequence.

Example 5 Classification of Reads of the Inbred Lines Progeny Population

Taking known rice genome Tiger (rapdb.dna.affrc.go.jp/) as a reference sequence, using alignment software such as SOAP (Li, R. et al. SOAP2: an improved ultrafast tool for short read alignment. Bioinformatics 25, 1966-7 (2009)), every individual read (2× Solexa data) of the inbred lines progeny population was aligned to the reference sequence. During aligning, a default parameter of SOAP software was used, without allowance of a vacancy, and allowing not more than 5 mismatches.

Figure 2:
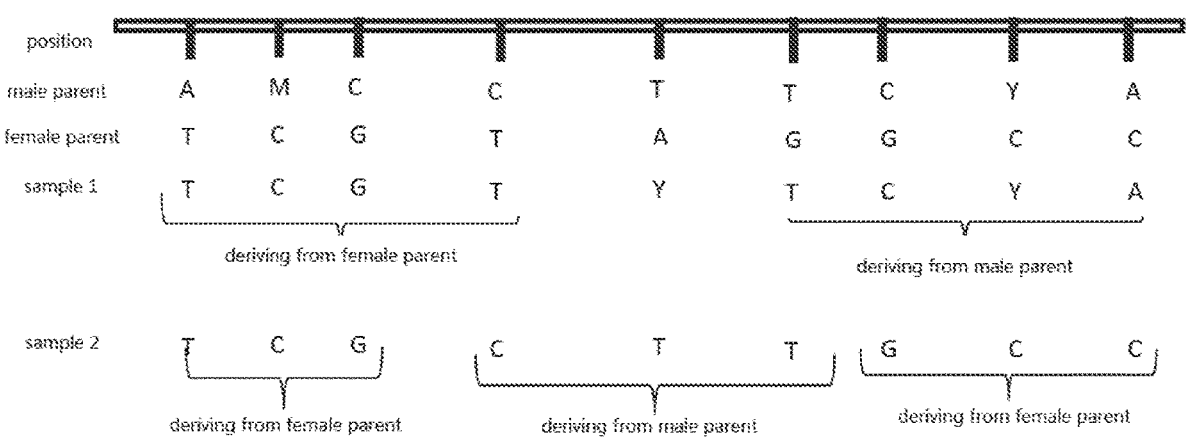
FIG. 2 schematically illustrates a principle and a method of determining a parent-of-origin of reads of progeny population. When a genotype of reads of progeny individuals at a segregation site is consistent with that of a male parent, the reads may be determined deriving from the male parent; and when a genotype of reads of progeny individuals at a segregation site is consistent with that of a female parent, the reads may be determined deriving from the female parent.

SOAPsnp software was used to analyze the aligned result obtained by SOAP software, so as to determine the genotype of every individual of the progeny population at every segregation site. According to genotype of parents at the segregation site and the genotype of progeny individuals at the segregation site, a base at every segregation site in the progeny individuals was able to be determined whether deriving from 9311 rice or PA64 rice, and every read of every progeny individual were able to be determining whether deriving from 9311 rice or PA64 rice. FIG. 2 schematically illustrated a principle and a method of determining a parent-of-origin of reads of progeny population. When a genotype of reads of progeny individuals at a segregation site was consistent with that of a male parent, the reads were able be determined deriving from the male parent; and when a genotype of reads of progeny individuals at a segregation site was consistent with that of a female parent, the reads were able be determined deriving from the female parent.

FIG. 6 schematically illustrated a parent-of-origin of a genotype of every individual in progeny population at a segregation site, in which 0 represented deriving from parent 9311 rice, 1 represented deriving from parent Pa64 rice, — represented being unknown and the first line (namely, BI4-BI18) represented No. of progeny individuals, the first column represented a physical position of the segregation site in a genome sequence.

Figures 7, 8:
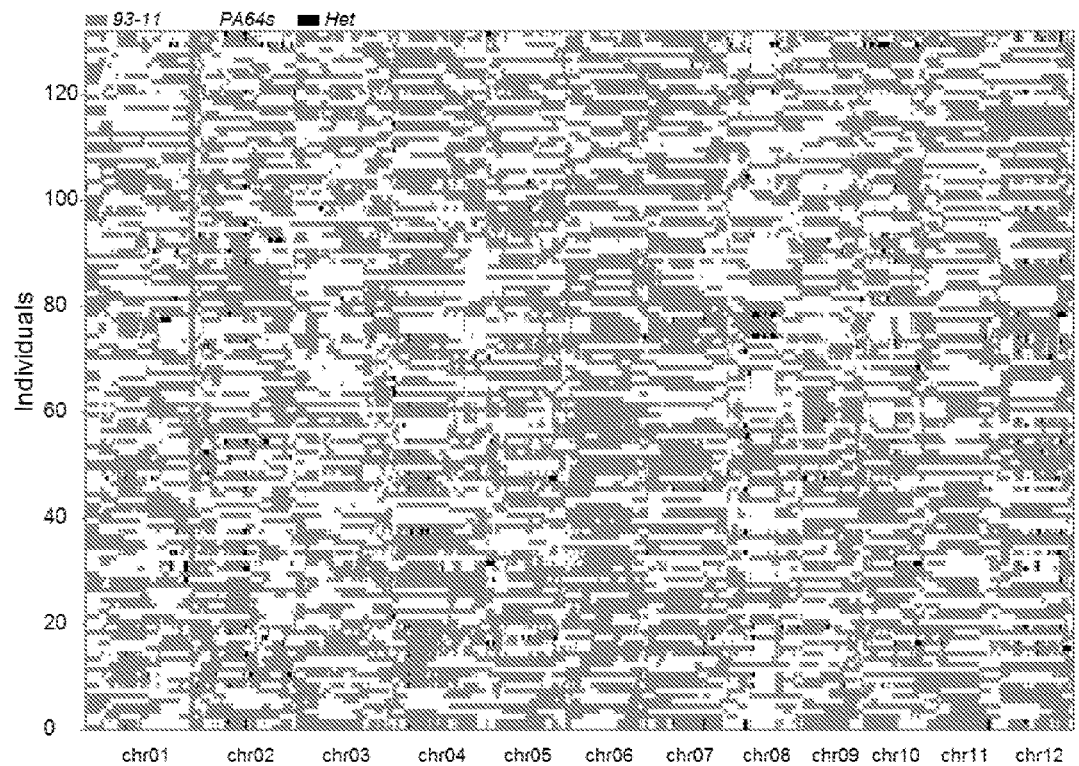
FIG. 7 shows a parent-of-origin of every progeny individual in every region on the whole genome level, in which chr01 to chr12 respectively represents chromosome 1 to 12, Het represents being heterozygous.
FIG. 8 schematically describes an assembling result of scaffolds of parent, in which the first line represents a meaning of: scaffolds with a No. Chr02_1 have a length of 13389 bp, which are accurately forward-located (+) to a position from site 283 to site 13670 in a linkage group chr02 (chr02_747m50) by 49 marker sequences; the second line represents a meaning of: scaffolds with a No. Chr02_2 have a length of 12902 bp, which are accurately forward-located (+) to a position from site 14188 to site 27101 in a linkage group chr02 (chr02_14344 m50) by 38 marker sequences; other lines represent similar meanings.

According to FIG. 6, a distribution of bases at every segregation site deriving from individual of parents in progeny individuals, then a recombination rate between the segregation sites was able to be calculated, and a genetic map was able to be obtained. In addition, as described above, it was able to determine from which parent every region of every individual in the inbred lines progeny population derived, according to FIG. 6. Such analyzed results were shown in FIG. 7. FIG. 7 showed a parent-of-origin of every progeny individual in every region on the whole genome level.

Figure 3:
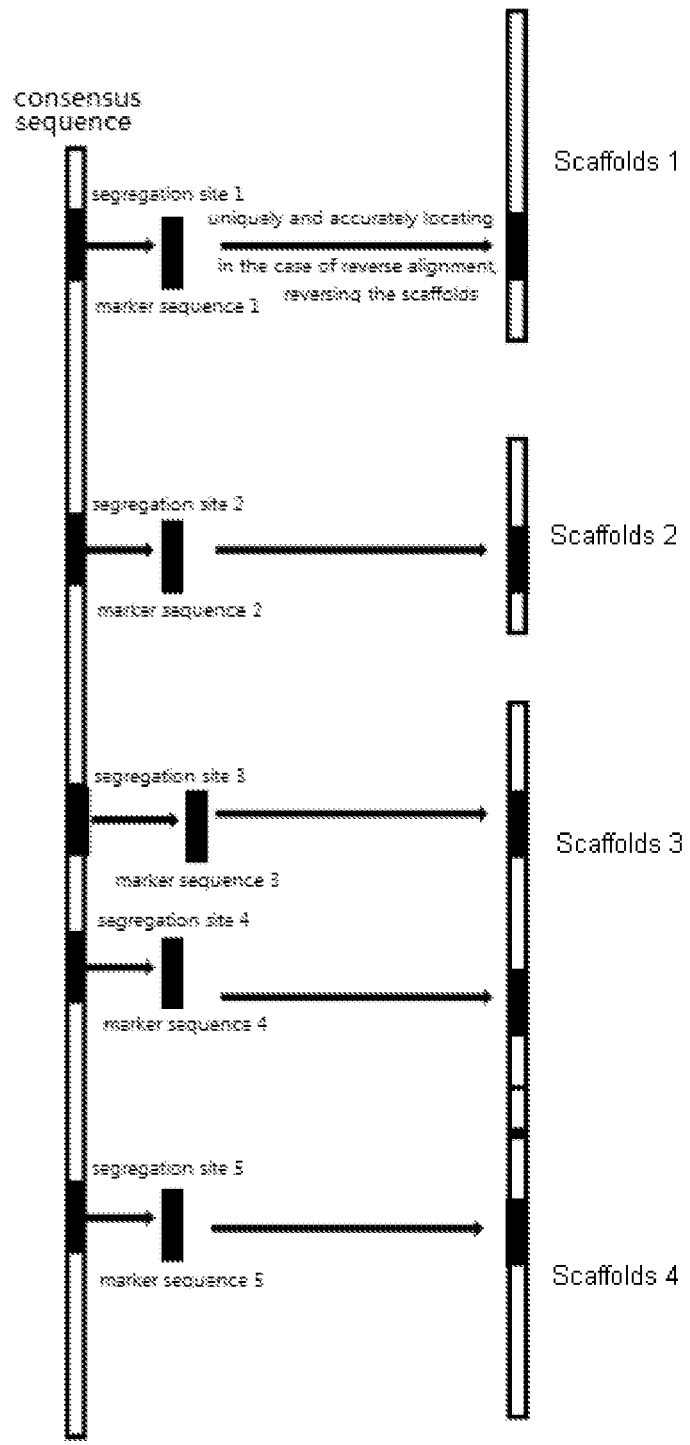
FIG. 3 schematically illustrates a method of assembling scaffolds of parents into a genome draft using a marker sequence.

Thus, by the above methods, reads of every progeny individual were able to be classified into following three categories:
1) reads deriving from 9311 rice
2) reads deriving from PA64 rice
3) undistinguishable reads Example 6 Anchoring Every Scaffold of Parents into a Corresponding Chromosome Linkage and Generating a Genome Draft As described in Example 4, every sequence located 50 bp before and 50 bp after the segregation site in respective consensus genotype sequence of the parents were selected as the marker sequence ((50 bp before the segregation site+the segregation site+50 bp after the segregation site=totally 101 bp), and the physical positions of these marker sequence in the Tiger genome were recorded. Using global alignment software Blastn (See for example nebc.nerc.ac.uk/bioinformatics/docs/blast+.html), these marker sequences were anchored into respective scaffolds obtained in Example 3 (the marker sequence should be uniquely and completely accurately aligned to the scaffolds). By means of the physical positions of these marker sequences in the Tiger genome, a sequence (namely, a position) and a distance among the scaffolds comprising the marker sequence were able to be determined, so as to assemble the scaffolds comprising the marker sequence, and further to obtain respective genome drafts of the parents. In the case of an unknown sequence presenting in the assembled scaffolds, an N region was used for connecting. Such procedure was schematically illustrated in FIG. 3.

FIG. 8 schematically describes an assembling result of scaffolds, in which the first line represents a meaning of: scaffolds with a No. Chr02_1 have a length of 13389 bp, which are accurately forward-located (+) to a position from site 283 to site 13670 in a linkage group chr02 (chr02_747 m50) by 49 marker sequences;

the second line represents a meaning of: scaffolds with a No. Chr02_2 have a length of 12902 bp, which are accurately forward-located (+) to a position from site 14188 to site 27101 in a linkage group chr02 (chr02_14344 m50) by 38 marker sequences.

According to the above information, positions of scaffolds with Nos of Chr02_1 and Chr02_2 were able to be known, and the N region between them was also known to be 518 bp (namely, 14188-13670), which was more accurate than the genetic map.

The statistical information of the assembling results of scaffolds of parents was also shown in Table 2.

TABLE 2

The statistical information of the assembling results of scaffolds of parents

| | Chromosome | | | All scaffolds | | |
|---|---|---|---|---|---|---|
| | number | Effective length (bp) | number of N region | number | Effective length (bp) | number of N region |
| PA64 | 12 | 322168935 | 39371 | 8098 | 347468362 | 41015 |
| 9311 | 12 | 366022060 | 44632 | 16403 | 410575626 | 48647 |

Example 7 Further Obtaining and Improving Genome Drafts of Parents Using Reads of Inbred Lines Progeny Population In order to sufficiently utilizing the reads of inbred lines progeny population, the present Example used following method of obtaining and improve the genome drafts of the parents, to finally obtain genomes of parent.

1. Obtaining and Improving the Genome Drafts of Parents Using New Scaffolds

Methods known in the art, for example SOAPDenovo assembly software (SOAP.genomics.org.cn/SOAPdenovo.html), the reads which had been determined parent-of-origin obtained in Example 5 were connected into new scaffolds (scaffolds new), namely, the reads which were identified deriving from 9311 rice in Example 5 were connected into new scaffolds of 9311 rice; the reads which were identified deriving from PA64 rice in Example 5 were connected into new scaffolds of PA64 rice.

As the genomes of inbred lines progeny population all derived from the parents, then the genome of the new scaffolds having a determined parent-of-origin of the inbred lines progeny population was consistent with the genome of the parents thereof. Therefore these new scaffolds were able to use in further improving and obtaining the genome sequence of the parents thereof.

Figure 4:
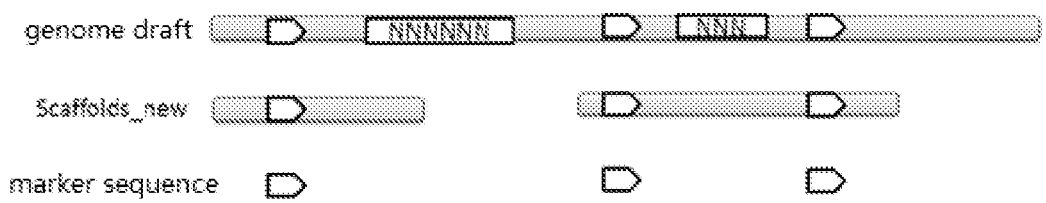
FIG. 4 schematically illustrates a method of locating new scaffolds of inbred lines progeny population on a genome draft of a parent using a marker sequence, and further obtaining and improving the genome draft of the parent by means of sequence information of the new scaffolds.

To locate and integrate these new scaffolds on the genome drafts of the parents, following method was used: continuous sequences having a length of 100 bp within 300 bp in the genome drafts of the parents were selected as a signing sequence, physical positions of these signing sequences in the genome drafts were recorded; using global alignment software Blastn, these signing sequences were anchored into the new scaffolds (the signing sequence should be uniquely and exactly accurately aligned to the scaffolds); by means of the physical positions of these signing sequences in the genome draft, the new scaffolds comprising the signing sequence were located in the genome draft. Such method schematically was shown in FIG. 4.

By the above method, most of the new scaffolds of 9311 rice and PA64 rice were able to be located in the genome draft of the corresponding parents (for example obtained in Example 6), then the sequence information of the new scaffolds was able to be used in further obtaining and improving the genome drafts of the corresponding parents (namely, genome sequence information).

2. Obtaining and Improving the Genome Drafts of the Parents by Means of a Pairwise Relationship of the Reads Deriving from the Inbred Lines Progeny Population In Solexa sequencing method, specific adaptors were ligated to the DNA fragments to be analyzed at both ends, then the obtained DNA fragments ligated to the specific adaptor at both ends were subjected to sequencing. Thus, the reads obtained by Solexa sequencing method were pairwise, having a pairwise relationship.

Figure 5:
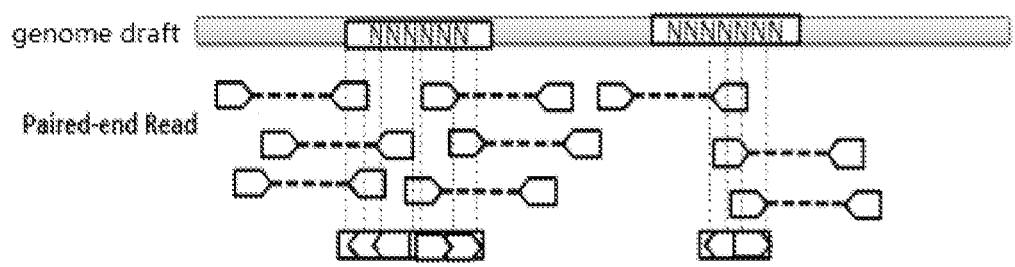
FIG. 5 schematically illustrates a method of further obtaining and improving a genome draft of a parent using reads of inbred lines progeny population having a pairwise relationship.

By means of the pairwise relationship, the genome drafts of the parents were able to be further obtained and improved, by the following method: after the parent-of-origin of the reads deriving from the progeny population was determined, paired reads were found, one of the paired reads was located around the non-N region in the genome draft of the corresponding parent, while the other one of the paired reads (or at least one part thereof) was located in the N region; the sequence information of the reads located in the N region (or at least one part thereof) was used in obtaining and improving the genome drafts of the corresponding parents (namely, genome sequence information). Such method was schematically shown in FIG. 5.

By the above method, after the parent-of-origin had been determined, the paired reads of the inbred lines progeny population were able to be used in improving the genome drafts of 9311 rice and PA64 rice obtained in Example 6.

3. Obtaining and Improving the Genome Drafts of the Parents by a Single Base Correction As the genomes of inbred lines progeny population all derived from the parents, then the genome of the reads having a determined parent-of-origin of the inbred lines progeny population was consistent with the genome of the parents thereof. Thereof, when the reads having the determined parent-of-origin of the inbred lines progeny population were aligned to the genome sequence of the corresponding parents which was selected as the reference sequence (namely, the above obtained genome draft), there was no SNP site (particularly a homozygous SNP site) theoretically. If a homozygous SNP site appeared, the genome sequence which was selected as the reference sequence could be considered as assembled with an error base at such site. In this circumstance, the base at this site in the genome sequence should be corrected as a base at the corresponding site in reads. Such procedure was known as single base correction herein.

Therefore, using SOAP and SOAPsnp software, the reads having the determined parent-of-origin of the inbred lines progeny population were aligned to genome sequences of 9311 rice and PA64 rice, to find the homozygous SNP site, and the genome sequences of the parents were subjected to the single base correction.

After obtaining and improving the genome drafts of the parents by the above method, the genomes of the parents were obtained. Furthermore, the scaffolds of the parents which had not located in the chromosome linkage group (namely, genome draft) in Example 6 were located in the obtained genomes of the parents. If the scaffolds of the parents were able to be exactly located in the genomes of the parents, it indicated that such scaffolds had been used for obtaining the genomes of the genomes by the above method, which should be removed. If the scaffolds of the parents were able to be partly located in the genomes of the parents, an overlapping relationship between such scaffolds and the genomes of the parents was able to assemble such scaffolds into the genomes of the parents.

The finally obtained statistical information of 9311 rice and PA64 rice was shown in Table 3.

TABLE 3

The finally obtained statistical information of 9311 rice and PA64 rice

|  | chromosome | | | all scoffolds | | |
| --- | --- | --- | --- | --- | --- | --- |
|  | number | effective length (bp) | number of N region | number | effective length (bp) | number of N region |
| PA64 | 12 | 351538699 | 46743 | 5166 | 370216171 | 47481 |
| 9311 | 12 | 369797235 | 43139 | 12730 | 408829591 | 44956 |

In Table 6, there were totally 36656 sites which had been subjected to the single base correction in PA64 rice genome; and there were totally 64596 sites which had been subjected to the single base correction in 9311 rice genome.

Finally, the finally obtained genomes of 9311 rice and PA64 rice were compared with the known rice genome Tiger. The compared result showed that the assembling level of the genomes of the parents had achieved the level of the known rice genome, which indicated that the method of the present disclosure was able to be used in rapid and effective assembly and obtaining genome with high accuracy.

Example 8 Apparatus for Implementing Examples 1 to 7

In order to implement the above examples 1 to 7, such apparatus was used, which comprised:

1) a sequencing unit, which was HiSeq 2000 sequencer (Illumina Company);

2) a data storing unit, for receiving and storing the data generated in Examples 1 to 7, being integrated into optiplex 380 desk computer (DELL Company);

3) a data processing unit, for processing the data generated in Examples 1 to 7, being integrated into optiplex 380 desk computer (DELL Company).

By using such apparatus, the present disclosure successfully used parents and sequencing data of inbred lines progeny population for assembly, to obtain genomes of parent 9311 rice and PA64 rice, and the accuracy and assembling level of the obtained genomes both achieved a level of known genome Tiger of rice, which had been proved in Examples 1 to 7.

Specific embodiments of the present disclosure have been described in details. However, it would be appreciated by those skilled in the art that: according to all disclosed teachings, various modifications and alternatives can be made to the details, and all these changes fall into the protective scope of the present disclosure. The full scope of the present invention is provided by the appended claims and any equivalents thereof.

What is claimed is:

1. A method of obtaining genomes of parents, wherein the parents consist of parent A and parent B, and the method comprises steps:

a) providing reads and scaffolds, comprising:

a1) subjecting the parents to a whole genome sequencing respectively, to provide the reads deriving from the parents, wherein the reads of the parent A constitute a database A0, the reads of the parent B constitute a database B0;

a2) connecting the reads in the database A0 into scaffolds of the parent A; and connecting the reads in the database B0 into scaffolds of the parent B, wherein the scaffolds of the parent A constitute a database A1, the scaffolds of the parent B constitute a database B1;

a3) providing inbred lines progeny population of the parents, wherein the inbred lines progeny population comprises at least one of inbred lines progeny individuals; and a4) subjecting every inbred lines progeny individual to the whole genome sequencing respectively, to provide paired reads of every inbred lines progeny individual, wherein the paired reads constitute a database C, namely, reads of the inbred lines progeny population;

b) identifying a segregation site of the parents, comprising:

b1) when other genomes of a species to which the parents belong are known, selecting a known genome as a reference sequence;

aligning the reads in the database A0 and the database B0 to the reference sequence respectively, to obtain consensus genotype sequences of the parent A and the parent B respectively;

comparing the consensus genotype sequences of the parent A and the parent B, to identify a different site presenting between the parents, namely, the segregation site;

determining a genotype of the parent A and parent B at the segregation site respectively; and recording a position of the segregation site in the reference sequence; or b2) when other genomes of a species to which the parents belong are unknown, selecting and assembling the reads deriving from one of the parents into an initial genome sequence as a reference sequence;

aligning the reads deriving from the other one of the parents to the reference sequence, to obtain a consensus genotype sequence of the parents respectively;

comparing the consensus genotype sequences of the parent A and the parent B, to identify a different site presenting between the parents, namely, the segregation site;

determining a genotype of the parent A and the parent B at the segregation site respectively;

recording a position of the segregation site in the reference sequence;

c) obtaining genome drafts of the parents, comprising:

c1) selecting a sequence located 10 bp to 90 bp before and/or 10 bp to 90 bp after the segregation site in the consensus genotype sequences of the parent A and the parent B as a marker sequence of the parent A and the parent B respectively, and recording a position of the marker sequence in the reference sequence in step b);

c2) locating the marker sequence of the parent A on the scaffolds in the database A1 and locating the marker sequence of the parent B on the scaffolds in the database B1 using a global alignment software, wherein the marker sequence should be uniquely and completely accurately aligned to the scaffolds located thereof; and c3) based on the position of the marker sequence in the reference sequence, arranging the scaffolds comprising the marker sequence in the database A1 and the database B1 in order, wherein an unknown sequence between two neighboring scaffolds is represented as an N-region, to obtain the genome drafts of the parent A and the parent B;

d) classifying the reads in the database C, comprising:

d1) aligning the reads in the database C to the reference sequence in step b), to determine whether these reads comprise the segregation site recorded in the reference sequence, and to determine a genotype thereof at the segregation site;

d2) based on the respective genotype of the parent A and the parent B at the segregation site in step d1), classifying the reads in the database C into 3 categories:
   i) reads of which the genotype at the segregation site is consistent with the genotype of the parent A, derives from the parent A, and constitute a database A2;
   ii) reads of which the genotype at the segregation site is consistent with the genotype of the parent B, derives from the parent B, and constitute a database B2;
   iii) undistinguishable reads; and
d3) connecting the reads in the database A2 into new scaffolds of the parent A, to constitute a database A3; connecting the reads in the database B2 into new scaffolds of the parent B, to constitute a database B3, and
e) obtaining the genome of the parent A and the parent B by following steps:
   e1) improving the genome drafts of the parent A using the scaffolds in the database A3 and improving the genome drafts of the parent B using the scaffolds in the database B3, comprising:
      e1-1) selecting a continuous sequence having a length of 50 bp to 150 bp within 200 bp to 400 bp of a non-N region sequence in the genome drafts of the parent A and the parent B as a signing sequence respectively, and recording a position of the signing sequence in the genome drafts;
      e1-2) locating the signing sequence of the parent A on the scaffolds in the database A3, locating the signing sequence of the parent B on the scaffolds in the database B3, wherein the signing sequence should be uniquely and completely accurately aligned to the scaffolds located thereof; and
      e1-3) based on the position of the signing sequence in the genome drafts,
         locating the scaffolds comprising the signing sequence in the database A3 in the position of the signing sequence in the genome drafts of the parent A,
         locating the scaffolds comprising the signing sequence in the database B3 in the position of the signing sequence in the genome drafts of the parent B, and
         filing up the N region in the genome drafts using the scaffolds comprising the signing sequence; and/or
   e2) improving the genome drafts of the parent A using a pairwise relationship between the reads in the database A2 and improving the genome drafts of the parent B using a pairwise relationship between the reads in the database B2, comprising:
      e2-1) finding paired reads having the pairwise relationship in the database A2, wherein one of the paired reads is located in the non-N region in the genome draft of the parent A, while at least one part of the other one of the paired reads is located in the N region; then filling up the N region in the genome draft of the parent A using the other one of the paired reads; and
      e2-2) finding paired reads having the pairwise relationship in the database B2, wherein one of the paired reads is located in the non-N region in the genome draft of the parent B, while at least one part of the other one of the paired reads is located in the N region; then filling up the N region in the genome draft of the parent B using the other one of the paired reads.

2. The method of claim 1, wherein the parent is a plant.

3. The method of claim 1, wherein in step a1), the parents have a whole genome sequencing depth of at least 30×.

4. The method of claim 1, wherein in step a1), the parents are subjected to the whole genome sequencing by a Solexa sequencing method.

5. The method of claim 1, wherein in step a2), the reads in the database A0 are connected into the scaffolds of the parent A using SOAPDenovo software using SOAPDenovo software; and
the reads in the database B0 are connected into the parent B using SOAPDenovo software.

6. The method of claim 1, wherein in step a3), the inbred lines progeny population comprises at least 200 or more of the inbred lines progeny individuals.

7. The method of claim 1, wherein in step a4), every inbred lines progeny individual has a whole genome sequencing depth of at least 4×.

8. The method of claim 1, wherein in step a4), every inbred lines progeny individual is subjected to the whole genome sequencing by a Solexa sequencing method.

9. The method of claim 1, wherein in step b1) or b2), the reads are aligned to the reference sequence using short sequence alignment software such as SOAP or bwa; analyzing an aligned result using SOAPsnp software, to obtain the consensus genotype sequence of the parent.

10. The method of claim 1, wherein in step c1), sequences located 50 bp before and 50 bp after the segregation site are selected as the marker sequence.

11. The method of claim 1, wherein in step c2), the global alignment software is Blastn.

12. The method of claim 1, wherein in step d1), short sequence alignment software such as SOAP or bwa is used for aligning, and SOAPsnp software is used for analyzing the aligned result.

13. The method of claim 1, wherein in step d3), the reads in the database A2 are connected to the new scaffolds of the parent A using SOAPDenovo software; and the reads in the database B2 are connected to the new scaffolds of the parent B using SOAPDenovo software.

14. The method of claim 1, wherein in the step e1-1), a continuous sequence having a length of 100 bp within 300 bp of the non-N region sequence in the genome drafts is selected as the signing sequence.

15. The method of claim 1, further comprising step (f) subjecting the genomes of the parents in step e) to a single base correction, comprising:
   f1) aligning the reads in the database A2 to the genome of the parent A, wherein the genome of the parent A is selected as a reference sequence; finding a homozygous SNP site; correcting a base of the genome of the parent A at the homozygous SNP site using a base of the reads at the homozygous SNP site; and/or
   f2) aligning the reads in the database B2 to the genome of the parent B, wherein the genome of the parent A is selected as a third reference sequence; finding a homozygous SNP site; correcting a base of the genome of the parent B at the homozygous SNP site using a base of the reads at the homozygous SNP site.

16. The method of claim 15, further comprising step (g), step (g) comprising steps:
   g1) aligning the scaffolds being not integrated into the genome draft of the parent A in the database A1 in step c3) to the genome of the parent A obtained in step f), wherein if the scaffolds can be located in the genome, the scaffolds are further used to obtain the genome; and/or g2) aligning the scaffolds being not integrated into the genome draft of the parent B in the database B1 in step c3) to the genome of the parent B obtained in step f), wherein if the scaffolds can be located in the genome, the scaffolds are further used to obtain the genome.

* * * * *